US00PP20958P2

(12) United States Plant Patent
Zerr

(10) Patent No.: US PP20,958 P2
(45) Date of Patent: Apr. 27, 2010

(54) POINSETTIA PLANT NAMED 'FISMIRWHI'

(50) Latin Name: *Euphorbia pulcherrima*
Varietal Denomination: Fismirwhi

(75) Inventor: Katharina Zerr, Höhr-Grenzhausen (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/322,398

(22) Filed: Feb. 2, 2009

(51) Int. Cl.
*A01H 5/00* (2006.01)

(52) U.S. Cl. ..... Plt./304

(58) Field of Classification Search ..... Plt./304, Plt./305
See application file for complete search history.

*Primary Examiner*—Kent L Bell
(74) *Attorney, Agent, or Firm*—S. Matthew Edwards

(57) ABSTRACT

A new Poinsettia plant named 'Fismirwhi' particularly distinguished by cream white flower color, large, flat inflorescences, dark green, weakly lobed foliage, well-branching, medium sized, mounding habit, and early flowering.

1 Drawing Sheet

Latin name of the genus and species of the plant claimed: *Euphorbia pulcherrima.*

Varietal denomination: 'Fismirwhi'.

BACKGROUND OF THE NEW PLANT

The present invention comprises a new Poinsettia plant, botanically known as *Euphorbia pulcherrima,* and hereinafter referred to by the variety name 'Fismirwhi'.

'Fismirwhi' is a product of a planned breeding program. The new cultivar 'Fismirwhi' has cream-white, moderately lobed bracts, dark green foliage, early flowering, and medium sized plant habit.

'Fismirwhi' originated from hybridizations made from late June to early August 2002 in a controlled breeding program in Hillscheid, Germany. The female parent was the commercial variety 'Fiselfi', U.S. Plant Pat. No. 13,736, with red, distinctly lobed bracts and dark green foliage.

The male parent of 'Fismirwhi' was the pollen mixture 'H', taken from a group of proprietary plants (unpatented breeding lines) with bright red bracts and dark green foliage.

'Fismirwhi' was selected as one flowering plant within the progeny of the stated cross in December 2003 in a controlled environment in Hillscheid, Germany.

The first act of asexual reproduction of 'Fismirwhi' was accomplished when vegetative cuttings were used from the initial selection in the spring of 2004 and grafted on rootstocks of the variety 'Maren', in order to improve the branching ability. Cuttings from the successfully grafted stems were used in the summer of 2005, rooted and cultivated for the first, small trial in fall and winter of 2005.

Horticultural examination of plants grown from cuttings of the plant initiated in the summer of 2005 in Hillscheid, Germany, and continuing thereafter on a larger scale, has demonstrated that the combination of characteristics as herein disclosed for 'Fismirwhi' are firmly fixed and are retained through successive generations of asexual reproduction.

'Fismirwhi' has not been observed under all possible environmental conditions. The phenotype may vary significantly with variations in environment such as temperature, light intensity and day length.

Plant Breeders' Rights for this cultivar were applied for in the European Union on Apr. 10, 2008 and in Canada on Jul. 4, 2008. 'Fismirwhi' has not been made publicly available more than one year prior to the filing of this application.

DESCRIPTION OF DRAWING

The accompanying photographic drawing shows typical flower and foliage characteristics of 'Fismirwhi' with colors being as true as possible with an illustration of this type. The photographic drawing is a flowering pot, taken on Dec. 1, 2008, with plants potted in mid July 2008, about 19 weeks old.

DETAILED BOTANICAL DESCRIPTION

The measurements were taken in Hillscheid, Germany, latitude 50°, in mid December 2008 on about 20 week old plants growing in a greenhouse. Culture of these plants had started in late July 2008 with planting rooted cuttings in 14 cm pots and pinching about 2 weeks later. The plants were grown under natural day light in the fall (no black cloth to initiate earlier flowering) and at the moderately warm temperature of 18° C. for the bench heating.

Color Chart used: Royal Horticultural Society Colour Chart (R.H.S.) 2001.

BRIEF SUMMARY OF INVENTION

The following observations, measurements, and comparisons describe plants grown on benches in a greenhouse in Hillscheid, Germany. The following traits have been repeatedly observed and are determined to be basic characteristics of the new variety. The combination of these characteristics distinguishes this Poinsettia plant as a new and distinct variety.

1. Cream-white, weakly lobed flower bracts
2. Relatively large, horizontally borne inflorescences
3. Dark green foliage, ovate, weakly lobed leaves
4. About medium vigor, compact, well-branched habit
5. Early flowering response

DIFFERENCES BETWEEN THE NEW VARIETY 'FISMIRWHI' AND SIMILAR VARIETIES

'Fismirwhi' has a similar bract color as 'Fisson White' (U.S. Plant Pat. No. 10,825), but differs by having a somewhat weaker degree of lobing of bract and leaf margins, and more horizontally borne bracts, while bracts of 'Fisson White' often slant downwards. Additionally, 'Fismirwhi' has a more evenly mounding plant habit and earlier flowering.

In contrast to 'Fismars Creme' (U.S. Plant Pat. No. 17,658), 'Fismirwhi' has a somewhat more compact plant habit, larger bracts with at least weak lobing, and earlier flowering.

Plant:

*Form, growth and habit.*—Low shrub, with the branches slanting upright at an angle of over 45 degrees, well-branched.

*Plant height* (*without pot*).—32 cm.

*Plant width.*—47 cm.

*Number of branches.*—6–7.

*Number of inflorescences.*—5–6.

Foliage:

*Arrangement.*—Alternate.

*Quantity.*—5–6 leaves per branch.

*Aspect.*—Most petioles are horizontally to slightly upward directed, while the leaf blades are horizontal to slightly downwards.

*Immature leaf color, upper surface.*—Grass-green, RHS 143B.

*Lower surface.*—Approximately RHS 144B.

*Mature, leaf color, upper surface.*—Dark green, RHS 137A to nearly 139A.

*Lower surface.*—RHS 137B.

*Leaf length.*—12–15 cm.

*Leaf width.*—9.5–11.5 cm.

*Shape.*—Ovate with a moderate degree of lobing, that is 'oak-leaf' shaped.

*Base shape.*—Nearly truncate to rounded.

*Apex shape.*—Acuminate.

*Margin.*—Entire, lobes are rounded or have acute tips.

*Texture.*—Flat, smooth, apart from the protruding veins on the under-side, glabrous.

*Color of veins, upper surface.*—Approximately RHS 8D to RHS 150C.

*Color of veins, lower surface.*—RHS 145B to 145C.

*Petiole color, upper surface.*—Yellowish green to light green, RHS 8C or 145C.

*Petiole color, lower surface.*—Light green, RHS 145C.

*Petiole length.*—6.5–8.5 cm.

*Diameter of petiole.*—0.3 cm.

*Texture upper and lower surfaces.*—Smooth, glabrous.

Stem:

*Color of stem.*—Green, near RHS 144A, no anthocyanin.

*Length of stem.*—Approximately 18–21 cm.

*Diameter.*—0.6–0.7 cm.

*Length of internodes.*—2–4 cm.

*Texture.*—Glabrous.

Inflorescence:

*Type.*—Terminal cyme with surrounding whorl of colored bracts.

*Flowering, botanically* (*opening of the stamina, shedding of pollen*).—In late November.

*Flowering period, commercially* (*sufficiently colored bracts*).—Around November 15.

*Flowering response time.*—About 7.5–8 weeks from equinox. Duration of flowering: Depends from light and environment, at least 4–8 weeks of 'shelf' life.

*Fragrance.*—Absent.

*Shape of inflorescence.*—Rosette-like arrangement, mostly flat and horizontally borne.

*Diameter of inflorescence.*—25–30 cm.

*Inflorescence, vertical diameter.*—2.5–5.0 cm.

*Number of completely colored bracts per inflorescence* (*sized over 2 cm*).—10–13.

*Single bract, shape.*—Ovate, weak to moderate oak-leaf-shape.

*Bract, apex.*—Acuminate.

*Bract, base.*—Acute to obtuse.

*Single bract, length of blade.*—13–15 cm, younger bracts diminishing in size.

*Single bract, width of blade.*—7.5–9.8 cm.

*Bract color, upper side.*—RHS 4D, cream white.

*Bract color, lower side.*—RHS 2D.

*Vein color, upper surface.*—From RHS 150C at the base to RHS 8D near the tip.

*Vein color, lower surface.*—Mainly RHS 145C, pale green.

*Bract petiole length.*—About 2–3.5 cm, shorter for the younger bracts.

*Bract petiole diameter.*—0.3 cm.

*Petiole color, upper surface.*—Ranging from RHS 8C, cream, to 145C, pale green.

*Petiole color, lower surface.*—Approximately RHS 145C.

*Texture.*—Flat, smooth to somewhat rugose.

Cyme (true inflorescence):

*Cyme, diameter.*—1.8–2.0 cm.

*Number of cyathia.*—Most often 5–7, borne in a tight cluster.

*Cyathium, shape.*—Ovate.

*Cyathium, diameter.*—0.5 cm.

*Cyathium, length.*—0.6–0.7 cm.

*Color.*—Mainly RHS 143C, top is RHS 4C, yellowish.

*Peduncle length.*—3–4 mm.

*Peduncle color.*—RHS 144C to 145D.

*Nectar cups.*—Usually one per cyathium.

*Nectur cup, width.*—Mostly 4 mm.

*Nectar cup, color.*—Golden yellow, RHS 13A, no anthocyanin, no red color at the margin.

Reproductive organs:

*Stamen* (*actually reduced male florets*).—Usually in a small bunch of 10–15 at the top of the cyathium.

*Shape.*—Strap-like.

*Filament length.*—3–4 mm.

*Filament color.*—Cream-white, RHS 2D.

*Anther color.*—Yellow, RHS 11A.

*Anther diameter.*—1 mm.

*Pollen quantity.*—Moderate (normal quantity).

*Pollen color.*—Yellow, RHS 12A.

*Pistils* (*actually female flowers*).—Sparse in mid winter, one per cyathium, occurrence depends much on light intensity, appears (if at all) about 4 weeks later than the stamen.

*Stigma shape.*—Trifurcate, 6-lobed.
*Style and stigma color.*—Cream, RHS 2D.
*Ovary shape.*—Ovate or obovate, 3 ovules.
*Ovary size.*—3 mm in diameter (probably larger in regions with higher light intensity).
*Ovary color.*—RHS 144A.
*Fertility/seed set.*—No seed set observed, but appears fertile.

Disease/pest resistance: Disease resistance or susceptibility has not been observed on this hybrid.

What is claimed is:

1. A new and distinct variety of Poinsettia plant named 'Fismirwhi', substantially as illustrated and described herein.

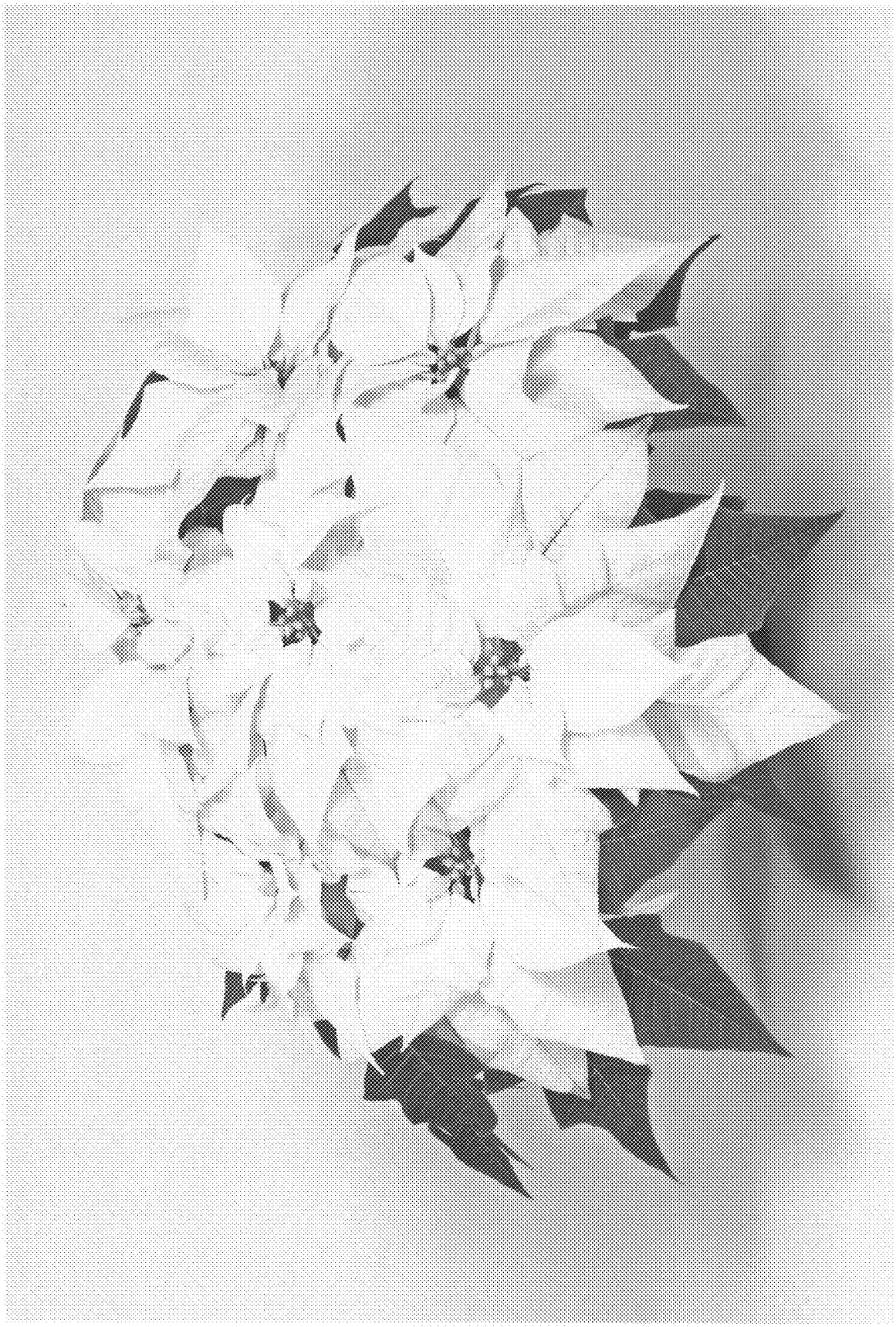

* * * * *